United States Patent [19]
Hughes

[11] Patent Number: 5,392,046
[45] Date of Patent: Feb. 21, 1995

[54] ENTROPY BASED SIGNAL, TRANSMISSION, RECEPTION AND SIGNAL ANALYSIS METHOD AND APPARATUS

[75] Inventor: Michael S. Hughes, Chesterfield, Mo.

[73] Assignee: Mallinckrodt Medical, Inc., St. Louis, Mo.

[21] Appl. No.: 108,525

[22] Filed: Aug. 19, 1993

[51] Int. Cl.$^6$ ............... G01S 13/08; G01V 3/12; G01V 3/38
[52] U.S. Cl. ................... 342/22; 342/126; 342/195; 342/197
[58] Field of Search ............ 342/22, 126, 189, 192, 342/193, 194, 195, 196

[56] References Cited

U.S. PATENT DOCUMENTS

| | | | |
|---|---|---|---|
| 4,481,517 | 11/1984 | Brown | 342/22 |
| 5,068,597 | 11/1991 | Silverstein et al. | 342/192 X |
| 5,097,331 | 3/1992 | Chen et al. | 358/138 |
| 5,107,841 | 4/1992 | Sturgill | 128/661.09 |

OTHER PUBLICATIONS

M. S. Hughes, "A comparison of Shannon entropy versus signal energy for acoustic detection of artificially induced defects in Plexiglas", J. Acoust. Soc. Am., 91(4), Pt. 1, Apr. 1992, pp. 2272–2275.
M. S. Hughes, "Analysis of Ultrasonic Waveforms Using Shannon Entropy", 1992 Ultrasonic Symposium, pp. 1205–1209.
M. S. Hughes, "Analysis of digitized waveforms using Shannon entropy", J. Acoust. Soc. Am. 93(2), Feb. 1993, pp. 892–906.
C. Bender and S. Orszag, Advanced Mathematical Methods for Scientists and Engineers, pp. 17–19.
D. Zwillinger, Handbook of Differential Equations, pp. 268–276.
D. Menzel, Fundamental Formulas of Physics, pp. 102–103.
E. L. Ince, Ordinary Differential Equations, pp. 254–263.

*Primary Examiner*—John B. Sotomayor
*Attorney, Agent, or Firm*—Rothwell, Figg, Ernst & Kurz

[57] ABSTRACT

An entropy based signal transmission, reception and analysis method and apparatus in which the entropy of time dependent signals is determined by utilizing a selected Green's function relationship. Information with respect to a medium with which the signals have interacted is derived by comparison of the entropies of the signals. In a preferred embodiment, the density distribution functions of selected digitized time segments of the signals to be analyzed are determined by utilizing the selected Green's function relationship and the entropies of the signals are then determined from the density distribution functions and compared with each other to derive the desired information.

24 Claims, 8 Drawing Sheets

ENTROPY BASED SIGNAL, TRANSMISSION, RECEPTION AND SIGNAL ANALYSIS METHOD AND APPARATUS

BACKGROUND OF THE INVENTION

This invention relates generally to apparatus and methods for analyzing and comparing signals, generally of the continuous waveform type, for the purpose of deriving information from the differences between the signals. Such analysis and comparison may be made, for example, with respect to signals which have been transmitted from a signal source through a medium for deriving information concerning the medium from the detected differences between the transmitted and received signals. Such differences in transmitted and received signals may occur, for example, as a result of certain characteristics of the medium which may include inhomogeneities and/or non-uniformities in the medium. More particularly, the present invention relates to the analysis and comparison of signals utilizing entropy based analytical apparatus and methods.

Types of apparatus and methods of the foregoing type include radar and sonar systems wherein continuous waveform signals are transmitted through media such as the earth's atmosphere or water and are used to probe these media for discontinuities representing objects, inhomogeneities or disturbances of various types. The use of probing signals for the identification of objects, inhomogeneities, discontinuities, non-uniformities or disturbances in wave propagation media has been known in the art for a wide variety of applications.

In prior art systems of this type, such as in early radar and sonar systems, it was common to utilize simple but effective square-law detection and envelope detection techniques. In later systems, so-called correlation processor systems, which computed the correlation of received signals with replicas of the transmitted signal, were utilized and were considered more effective for some applications in extracting the returning signals from background noise and other forms of interference.

The square-law detector, the envelope detector and the correlation detector all share a common attribute in that they all calculate a quantity proportional to the energy of the received signal. In the case of received signals that are replicas of the transmitted signal which are obtained, for example, by reflection from a plane surface, the measurement of signal energy as the means of detection yields, according to well supported theory, the highest possible signal to noise ratios possible for a linear time-shift-invariant signal processing algorithm. However, recent experimental results have indicated that entropy measurements are significantly more effective than energy measurements as a means for detecting and analyzing the characteristics of the received signals.

In this respect, the utility of entropy imaging has been disclosed, for example, in the following scientific papers: (1) "Analysis of digitized waveforms using Shannon entropy" by M. S. Hughes, JASA 93(2), Feb. 1993, pp 892–906, (2) "A comparison of Shannon entropy versus signal energy for acoustic detection of artificially induced defects in Plexiglass" by M. S. Hughes, JASA 91(4) Pt.1 April 1992, pp 2272–2275 and (3) "Analysis of Ultrasonic waveforms using Shannon entropy", by M. S. Hughes, Proceedings IEEE UFFC symposium 1992, pp 1205–1209, all of which were authored by the present inventor and which are incorporated herein by reference. Apparatus and methods for such entropy based signal analysis techniques are also disclosed in U.S. patent application Ser. No. 07/906,571 entitled ENTROPY-BASED SIGNAL RECEIVER filed Jun. 30, 1992, in the name of the inventor of the subject matter of the present application, Michael S. Hughes.

In such previously reported entropy based systems and methods, it is necessary to calculate the "density distribution function" w(y) of the signal being analyzed in order to determine its entropy. A rigorous definition of w(y) is given in the paper of reference (1) above and is also explained further in the other references noted. The density distribution function w(y) is, in very general terms, a measure of how often in a selected time period chosen for purposes of analysis the function being analyzed takes on a selected value $Y_1$. For purposes of making such calculations, the signal waveform being analyzed is first digitized over the selected time interval in which the analysis is to be made. Then, as described in the references given above, a Fourier series approach is used to calculate the function w(y).

In such Fourier series based methods, it was found necessary to compute the density distribution function w(y) over an interval greater than the actual range of the received time dependent signal f(t), that is, over a range greater than $[f_{min}, f_{max}]$ of f(t). This was found necessary in order to prevent edge effects from corrupting the estimate of w(y) over the actual range $[f_{min}, f_{max}]$ of f(t). This imposes additional computational burdens on the apparatus and methods based on the Fourier series approach.

Secondly, the size of the computation required in the Fourier series approach is governed primarily by (1) the number of terms $N_{co}$ in the Fourier series required to represent w(y) and (2) the number of digitized points $N_\alpha$ used to represent the underlying continuous waveform. More precisely, the Fourier series approach requires the evaluation of $N_{co} \times N_\alpha$ double precision sums. This requires a substantial computational size for most applications.

A typical Fourier series method as previously reported is illustrated in steps 146 through 156 in the flow diagram FIG. 8. The details of the steps presented in FIG. 8 are disclosed in the previously published work of the present inventor and no further explanation of these steps is therefore required.

Thus, the Fourier series entropy based approach, while yielding acceptable results for most applications, requires a substantial computational size for its implementation. Certain other aspects of the Fourier series approach will also be further analyzed below.

SUMMARY OF THE INVENTION

The present invention provides an apparatus and method for transmitting, receiving and analyzing, utilizing entropy based techniques, various types of signals, such as continuous time dependent signals, in which a Fourier series representation of the signals being analyzed is not required. The present invention provides a substantial reduction in computational size for its implementation and produces the same or even higher image contrast as the previously used Fourier series approach in a computational time that is about three orders of magnitude smaller than the Fourier series method. The enormous increase in speed provided by the present invention is due, at least in part, to the fact that the present invention has a greater immunity to noise and to the fact that the number of calculations required is much smaller than in the previously used Fourier series approach.

The present invention utilizes, in one preferred embodiment thereof, a signal analysis technique which is based on a Green's function relationship for the computation of the density distribution function w(y). In this technique, the reconstruction of the density distribution function w(y) is limited to the actual interval of f(t), $[f_{min}, f_{max}]$, of the signal y=f(t), which results in a substantially more efficient computation. Secondly, the technique of the present invention avoids reliance on series approximation and is thereby effected with a substantially reduced number of double precision comparisons. The present invention therefore provides apparatus and methods which are much faster than and which produce fully equivalent or superior results than prior apparatus and methods utilizing entropy based techniques.

For example, in tests conducted with the Fourier series based entropy method as applied to experimental data acquired from a Plexiglass specimen having five machined "defects" to produce an entropy function image, thirty percent gains in pixel image contrast between defects and defect-free baseline regions was obtained over previously reported energy based systems. However, an execution time of about 26 hours on a network of thirty Digital Equipment Corporation Model 240 computer work stations was required to obtain the results. Using the method and apparatus of the present invention, the same results may be obtained with a relatively short run time on a Quadra 950 based personal computer.

DETAILED DESCRIPTION OF THE INVENTION

Figure 1:
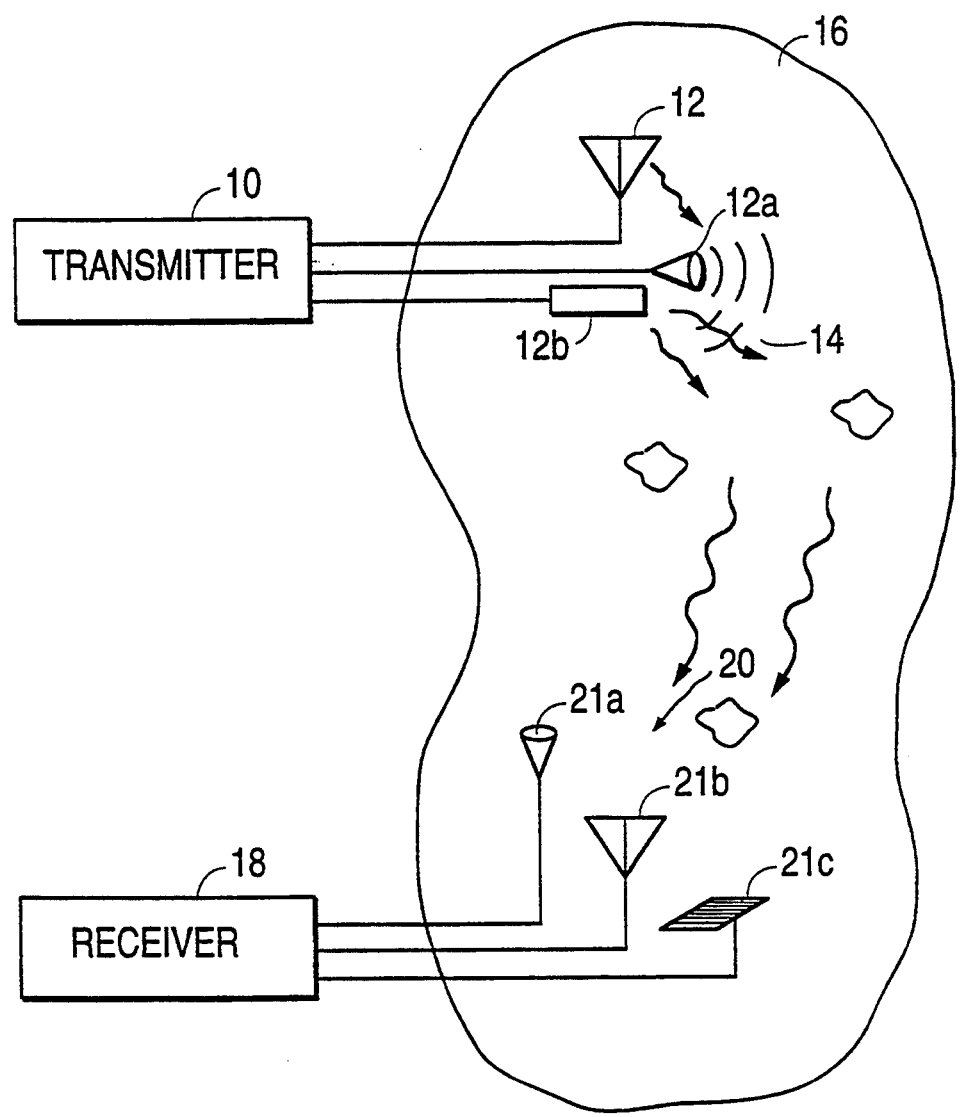
FIG. 1 is a block diagram of an entropy based signal transmission, reception and signal analysis apparatus embodying the present invention.

Referring to the block diagram of FIG. 1, there is shown a transmitter 10, which generates and transmits by means of a signal emission device, such as an antenna 12 for electromagnetic radiation, a transducer 12a for acoustic wave emission or a light emission device 12b for an optical signal, a signal 14 for transmission through a medium 16. The signal 14, which may be in the form of an electromagnetic signal (including light of any wavelength) or an acoustic signal, is preferably emitted in either a continuous or pulsed waveform for transmission through the medium 16.

The system includes a receiver 18 which receives and analyzes a received signal 20, after the signal has traveled through the medium 16 and has been altered or modified by structural or compositional discontinuities or non-homogeneities 22 present in the medium 16. The received signal may be detected by means of various different types of receiving apparatus such as, for example, an acoustic receiving transducer 21a, an antenna 21b or an x-y grid of light receiving pixels 21c, depending upon the nature of the transmitted signal. The signal 14 may interact with the medium 16 either by transmission through the medium or by reflection from the medium or through some other form of interaction. In order to make the necessary analysis of the received signal 20 for the purpose of determining the entropy thereof, the density distribution function w(y) of the received signal 20 is determined. The methodology of utilizing w(y) to determine the entropy of the signal is described in detail in the above references.

In accordance with a preferred embodiment of the present invention, the analysis of the received signal 20 to determine w(y) is carried out utilizing a Green's function approach to the analysis instead of the computationally intensive Fourier series approach of the previously reported methods and apparatus. As noted above, this provides a truly remarkable reduction in the computational size required for its implementation and produces the same or even higher image contrast as the previously used Fourier series approach. In a typical embodiment of the present invention, the computational time required was about three orders of magnitude smaller than the Fourier series method with fully equivalent or superior results than previously known Fourier series based apparatus and methods utilizing entropy based techniques.

Figure 2:
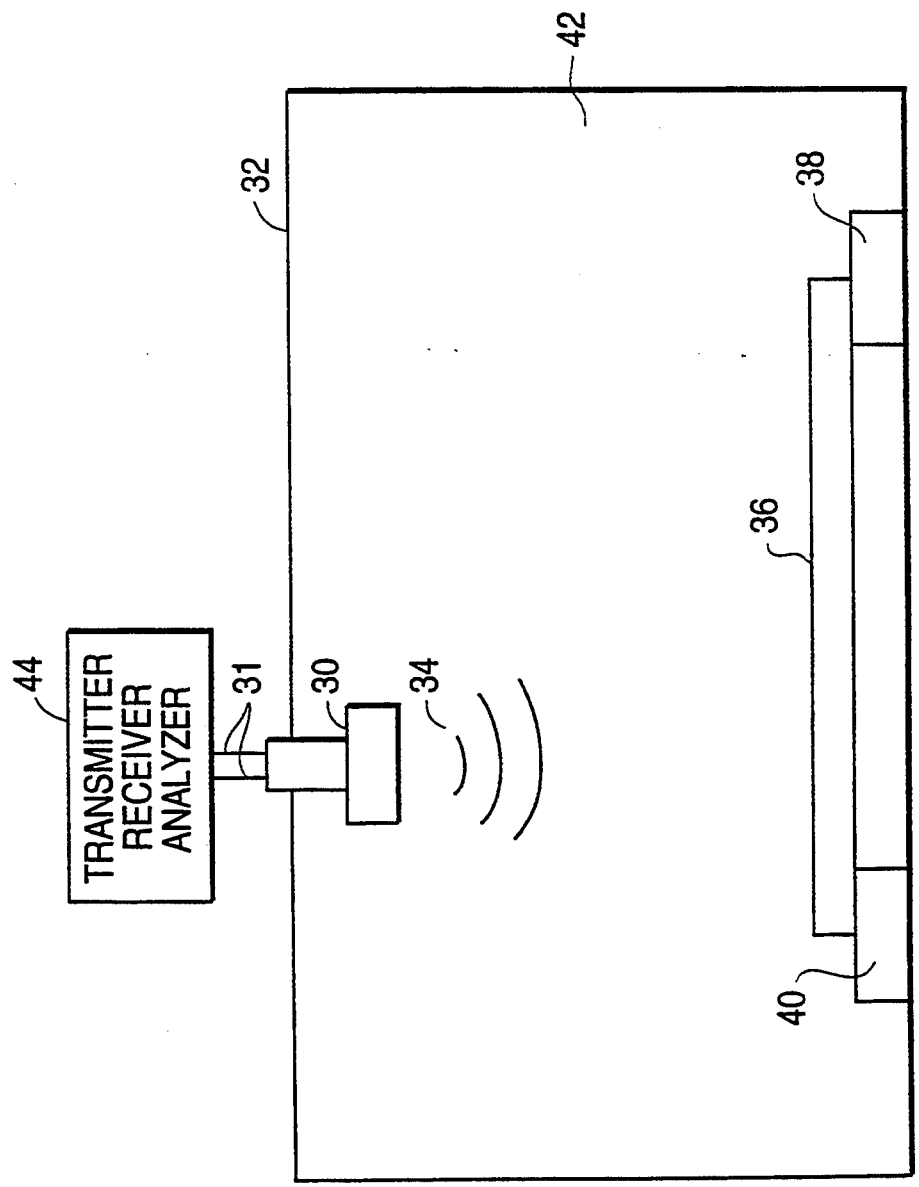
FIG. 2 a schematic illustration of an acoustic medium probing apparatus embodying the present invention.

FIG. 2 is a schematic of an acoustic probing and detection apparatus embodying the present invention. In the embodiment of FIG. 2, a narrow beam acoustic transducer 30 is positioned at the top of a test tank 32 and emits a downward directed narrow acoustic beam 34 which impinges on a test specimen 36 mounted on supports 38 and 49 at the bottom of the tank 32. The transducer 30 operates alternately in a transmission and reception mode. Acoustic signals are emitted in the form of pulses from the transducer 30 in response to electrical signals at the input/output terminals 31. The resulting echoes from the test specimen 36 are received by the transducer 30 and converted to electrical signals at the input/output terminals 31. The test tank 32 is preferably filled with a sound transmitting fluid 42 such as water for transmission of the acoustic beam 34 from the signal generator 30 to the test specimen 36.

A three dimensional determination of voids and other defects in the test sample 36 is obtained by analysis of the differences in the entropies of the transmitted and received acoustic signals. The entropies of the transmitted and received acoustic signals are determined by a transmitter/receiver/analyzer 44 utilizing Green's function in accordance with the present invention. Further details as to the construction and operation of the transmitter/receiver/analyzer 44 are set forth below.

In applications such as that shown in FIG. 2, it is usually unnecessary to analyze the transmitted signal since the information being sought from the analysis is comparative only as between a plurality of received signals reflected from selected points on a test area of a test specimen. For example, in the case where a test specimen is scanned and readings of the received signals are taken at selected locations over a test area in a test specimen, in some cases typically in the form of pixels arranged in an x-y grid, it is necessary only to compare the entropies of the received signals on a pixel by pixel basis to develop a contrast pattern of the relative gray scales of the pixel locations over the area being scanned. In such an application, the entropy values can be normalized for comparison and the portrayal of a photographic image or an image scanned onto a display for viewing and analysis.

The present invention utilizes Green's function to determine the entropy of the signals. Green's function and the methods for its derivation are well known in the art and applicable enabling references may be found in the literature. For example, one such reference is the book "Ordinary Differential Equations" by E. L. Ince, published 1956 by Dover Press, which provides an extensive analysis of Green's functions in Chapter XI thereof. Another such reference is Fundamental Formulas of Physics, § 21.7, edited by Donald H. Menzel, published by Dover Press in 1960.

In the method of the present invention, as generally depicted in FIG. 1, the entropies of the transmitted signal 14 and the received signal 20 are determined utilizing Green's functions and these entropies are then compared for purposes of analysis of the effects of the transmission of the signal through the medium 16 and the determination therefrom of the nature of the inhomogeneities in the medium 16. For purposes of explanation, the analysis of and the determination of the entropy Hc of the received signal 20 will be presented, it being understood that the analysis of and determination of the entropy of the transmitted signal 14 is carried out in the same manner.

As noted in reference (1) cited above, the entropy of the signal to be analyzed is preferably determined based on a modified definition of the well known Shannon entropy. This modified definition uses the term Hc to define the useful part of the Shannon entropy in the continuous limit. On this basis, for a signal represented by the continuous waveform y=f(t), Hc is defined as follows:

$$Hc \equiv \frac{1}{b-a} \int_\alpha^\beta w(y) \log_2[w(y)] dy \qquad \text{Eq. [1]}$$

Detailed definitions of the terms used in equation [1] are given in reference (1). As described in reference (1), Hc can be determined from the time dependent function y=f(t) using numerical techniques. Computationally, the most intensive portion of the calculation of Hc is the determination of the density distribution function w(y). This is carried by a method which is based on the equation:

$$\int_a^b \phi[f(t)] dt = \int_\alpha^\beta \phi(y) w(y) dy, \qquad \text{Eq. [2]}$$

which may be shown to hold for any continuous Φ using methods from real analysis. The advantages of using the defined metric Hc over the Shannon entropy H are also given in reference (1). As outlined above and in the references, the difficult part of determining Hc from this defined meaning is the calculation of the density distribution function w(y). In accordance with a preferred embodiment of the present invention, w(y) is determined, as will be set forth in greater detail below, by utilizing the Green's function:

$$G(y, \psi) = \begin{cases} (1 - \psi) y \text{ if } y \geq \psi \\ (1 - y) \psi \text{ if } \psi \geq y \end{cases} \qquad \text{Eq. [3]}$$

In general terms, for a signal which can be represented by a linear differential equation with linear boundary conditions, Green's function is a transfer function which yields an exact solution in the form of an integral. While the methods for determining Green's function are well known and are presented in the above cited references, among other references, the methodology of the present invention will be set forth for a particular embodiment thereof.

To begin the signal analysis in accordance with the method of the present invention, a time segment of the signal to be analyzed is selected and is converted from analog to digital form. After the selected time segment of the signal is digitized, a Green's function for an arbitrary linear differential operator with boundary conditions and domain of definition is chosen. The selection of this differential operator is completely a matter of choice and those skilled in the art will fully understand the basis for this selection. However, several guidelines can be used to determine the best choice for the particular signal to be analyzed. The most important of these guidelines are the immunity to noise and the speed of calculation of the Green's function which is uniquely determined by the differential operator and the boundary conditions and domain of definition. There is a one to one correspondence between differential operators with boundary conditions and Green's functions. For purposes of disclosure of one embodiment of the present invention, the differential operator $L=d^2/dy^2$ will be chosen with boundary conditions $u(0)=u(1)=0$ and domain of definition [0,1].

The choice of this Green's function permits Hc to be more rapidly determined than in the Fourier series approach. This speed improvement arises because the resulting computational scheme obtains w(y) from the second derivative of a quantity u(y) which is obtained from an integral of f(t). This integral may be approximated to arbitrary accuracy using the sampled version of f(t), denoted by $f_k$, k=0, 1, ... Nα.

For some choices of Green's function, the computation of u(y), and hence w(y), can be just as computationally intensive as in the Fourier series approach. However, for the Green's function chosen for this example and representing a preferred embodiment of the present invention, the computational complexity of the u(y) calculation can be reduced by several orders of magnitude, for most Nα of interest, if $f_k$ is first sorted into either ascending or descending order, either choice being acceptable. In a preferred embodiment of the present invention, the sort which is employed is known as a "qsort", which is a sorting technique well known in the art. It is only for this selected Green's function that this reordering is a practical mathematical operation.

We begin by considering a general differential operator L acting on a function u(y). The selected differential operator is:

$$Lu(y) = d^2 u(y)/dy^2 \qquad [4]$$

with boundary conditions $u(0)=u(1)=0$ and domain of definition being the interval $[0,1]$. With this domain, boundary conditions and differential operator L, the Green's function is:

$$G(y, \psi) = \begin{cases} (1 - \psi)y & \text{if } y \geq \psi \\ (1 - y)\psi & \text{if } \psi \geq y \end{cases} \quad \text{Eq. [5]}$$

All solutions to the second order differential equation $$Lu(y) = w(y) \quad \text{[6]}$$

where $w(y)$ is the density distribution function of $y=f(t)$, may now be expressed as $$u(y) = \int_\alpha^\beta G(y, \psi)w(\psi)d\psi \quad \text{Eq. [7]}$$

where the interval $[f_{min}, f_{max}]$ is contained in the interval $[\alpha, \beta]$. It is noted that since $y=f(t)$ takes on no values outside of $[f_{min}, f_{max}]$, $w(y)$ is necessarily zero outside of this interval so that in fact we have:

$$\int_\alpha^\beta G(y, \psi)w(\psi)d\psi = \int_{f_{min}}^{f_{max}} G(y, \psi)w(\psi)d\psi \quad \text{Eq. [8]}$$

wherein we allow $\alpha$, $\beta$ to be different from $f_{min}$, $f_{max}$ merely to preserve notational conventions established in previous work referred to herein where $w(y)$ was computed using a Fourier series and it was necessary to force $\alpha < f_{min}$ and $\beta > f_{max}$ in order to exclude ringing effects in the Fourier reconstruction of $w(y)$. Thus, if $u(y)$ is known, we merely compute $Lu(y)$ to find $w(y)$.

It might at first be thought that this is of no consequence since $u(y)$ can be calculated from $w(y)$ and, in order to do this, $w(y)$ must be known in the first place. However, using equation [2] from above, which is:

$$\int_a^b \phi[f(t)]dt = \int_\alpha^\beta \phi(y)w(y)dy, \quad \text{Eq. [9]}$$

we may then rewrite equation [7] as follows:

$$u(y) = \int_a^b G(y, f(t))dt, \quad \text{Eq. [10]}$$

from which $u(y)$ may be computed solely from knowledge of $f(t)$, which is measured, and $G(y,\psi)$, which is selected from the choice of L together with boundary conditions and domain of definition.

In practice, the integral in equation [10] is approximated by a discrete sum using a digital computer and a digitally sampled version of $f(t)$ given by $f_k$, $k=0, 1, \ldots N\alpha$. In this setting, one further refinement is possible in the computation if we use the Green's function of equation [5]. Namely, if we first sort the $f_k$ into either increasing or decreasing order, either choice being acceptable, the integrations in equation [10] can be accomplished using a running sum instead of recomputing the entire integral from scratch for each value of y. It is this reordering which contributes to the tremendous speed improvement attained by the present invention.

This reordering is only possible by first recasting the computation of $w(y)$ in terms of an integral of $f(t)$. Furthermore, by recasting the computation of $w(y)$ in terms of an integral of $f(t)$, we gain the further benefits of noise cancellation as different values of $f(t)$ with different (and on average cancelling) values of noise are added together during the integration process. This noise cancellation permits further reduction in computational complexity since it permits $u(y)$ and hence $w(y)$ to be accurately determined with a coarser grid than is required, for instance, in the Fourier series approach.

This outlines the general approach. The general Green's function approach of one embodiment of the present invention to computation of the density distribution function $w(y)$ is set forth in the flow diagram of FIG. 3. In step 100, the signal $y=f(t)$, whose entropy is to be determined, is received by the receiver 16 shown in FIG. 1. In step 102, the time segment of the signal $y=f(t)$ is selected for analysis. This is the selected time period from $t_1$ to $t_2$ over which the received signal is to be analyzed.

In step 104, the selected time segment of the signal $f(t)$ is digitized over the selected time period from $t_1$ to $t_2$. This is done by means of a sampling type analog to digital converter which quantizes the analog signal to a digital signal. The sampling rate is selected so as to provide the resolution required for the type of signal being analyzed and is preferably selected at the Nyquist rate. Steps 102 and 104 may be performed in any order. That is, the signal may be digitized first and then the time segment selected or vice versa.

Figure 3:
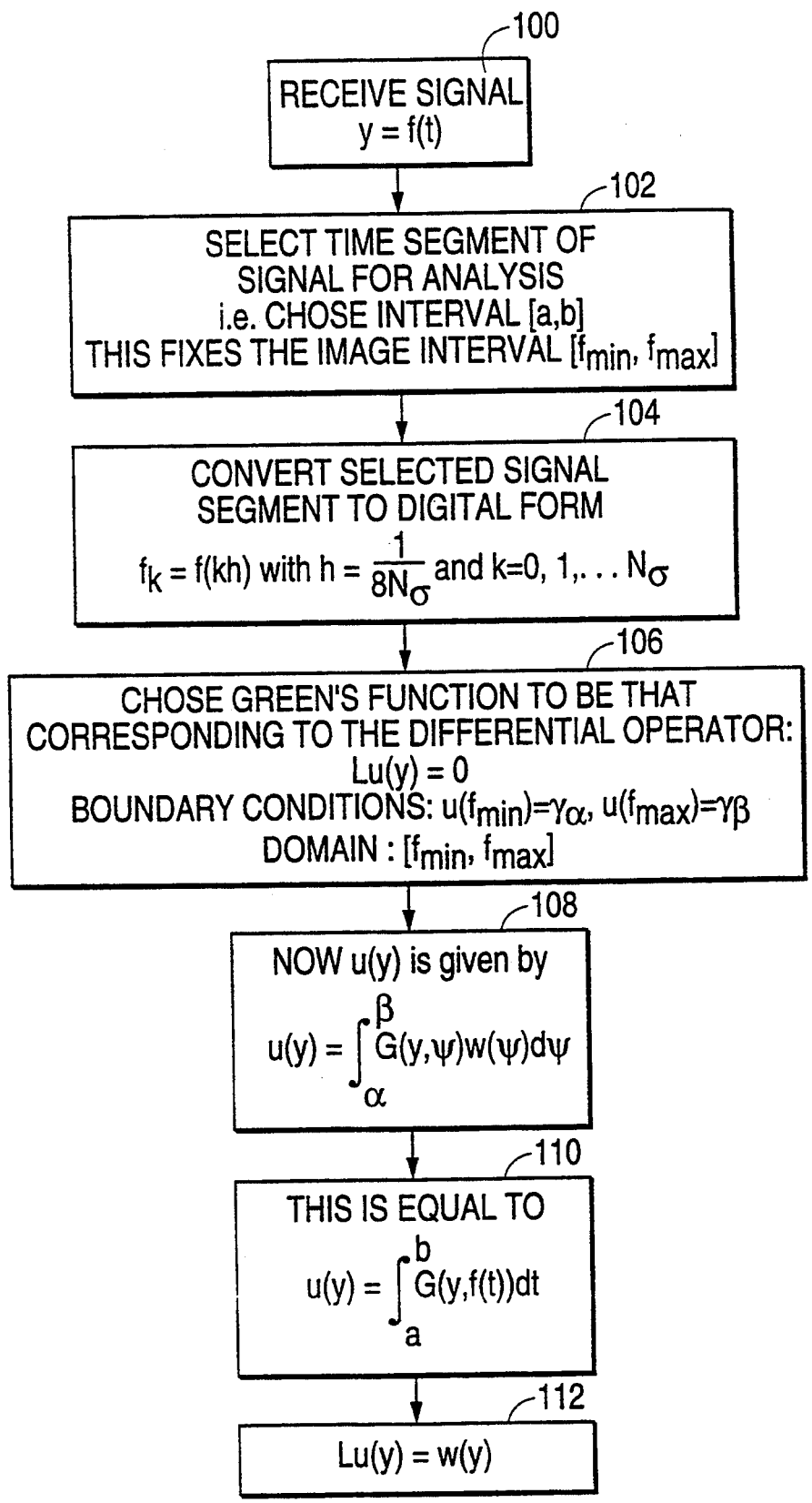
FIG. 3 is a flow diagram outlining the general Green's function approach of one embodiment of the present invention to computation of the density distribution function w(y)
Figure 4:
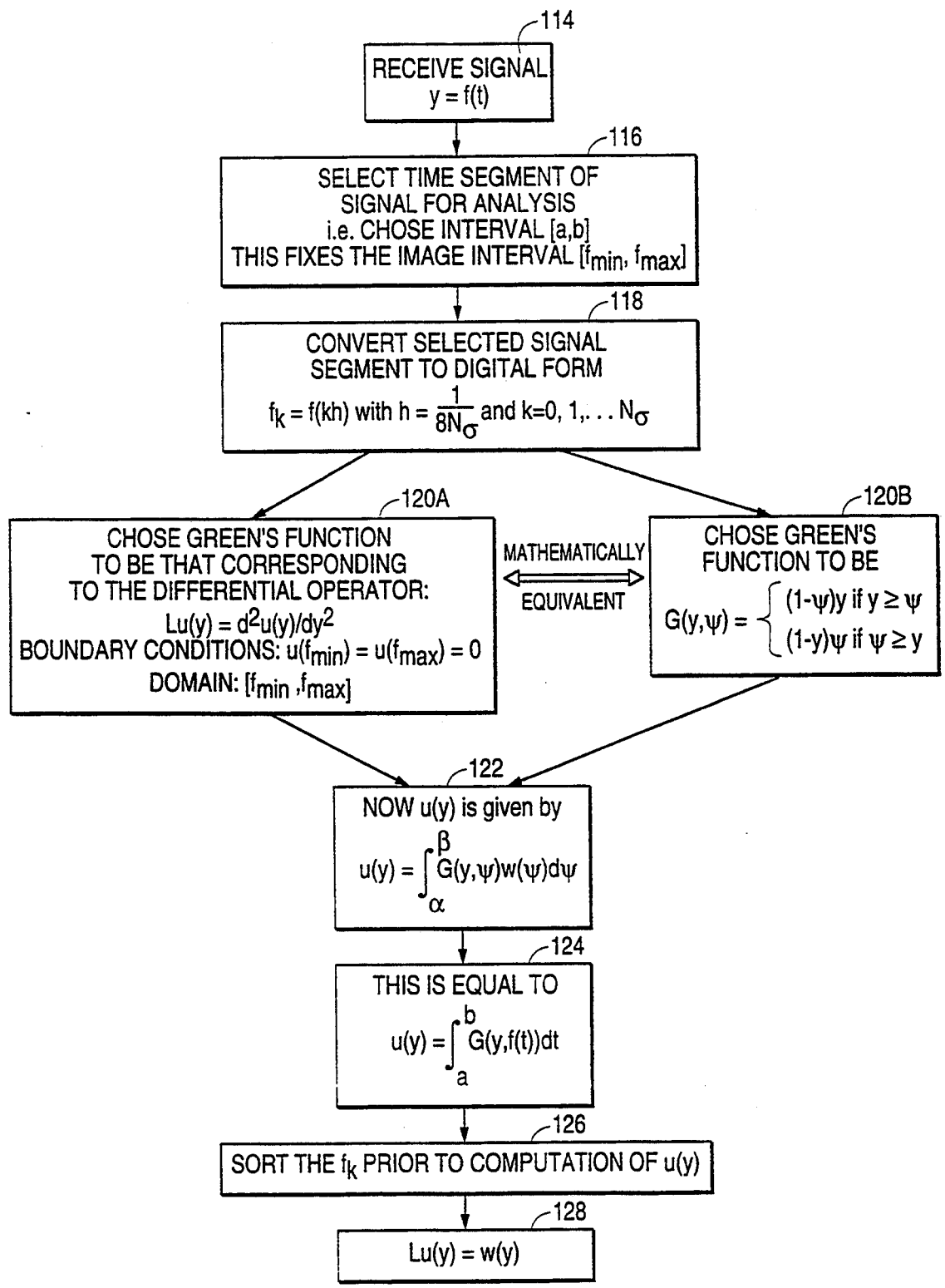
FIG. 4 is a flow diagram outlining an accelerated Green's function approach of the present invention.

In step 106, Green's function is selected using techniques as just described. In the general approach illustrated in FIG. 3, in step 106 Green's function is chosen to be that corresponding to $Lu(y)=0$, where L is any linear differential operator. Then, in step 108, the function $u(y)$ is given by:

$$u(y) = \int_\alpha^\beta G(y, \psi)w(\psi)d\psi,$$

which, as determined in step 110, is equal to:

$$u(y) = \int_a^b G(y, f(t))dt,$$

which leads in step 112 to $Lu(y)=w(y)$, the desired density distribution function. FIG. 4 is a flow diagram of the accelerated Green's function approach of the present invention. Initial steps 114, 116 of FIG. 3 and 118 are the same as steps 100, 102 and 104 of the flow diagram of FIG. 2 just described. Green's function is then chosen in one of the alternative and mathematically equivalent steps 120A or 120B based on the differential operator $Lu(y)=d^2u(y)/dy^2$ (step 120A) or, as shown in step 120 B, $G(y,\psi)=(1-\psi)y$ if $y \geq \psi$ or $G(y,\psi)=(1-y)\psi$ if $\psi \geq y$.

Once Green's function is chosen in step 120A or 120B, then in step 122 $u(y)$ is given by:

$$u(y) = \int_\alpha^\beta G(y, \psi)w(\psi)d\psi,$$

Then, in step 124, $u(y)$ is equal to:

$$u(y) = \int_a^b G(y, f(t))dt,$$

In step 126, the sampled version of f(t) given by $f_k$, k=0, 1, ... $N\alpha$ is sorted into either increasing or decreasing order, either choice being acceptable, prior to the computation of u(y). This sorting step is described above. Then, w(y) is determined in step 128 using a running sum instead of recomputing the entire integral from scratch for each value of u(y). As noted above, the reordering step 126 contributes to the tremendous speed improvement attained by the accelerated Green's function approach of the embodiment present invention illustrated in the flow diagram of FIG. 4.

Figure 5:
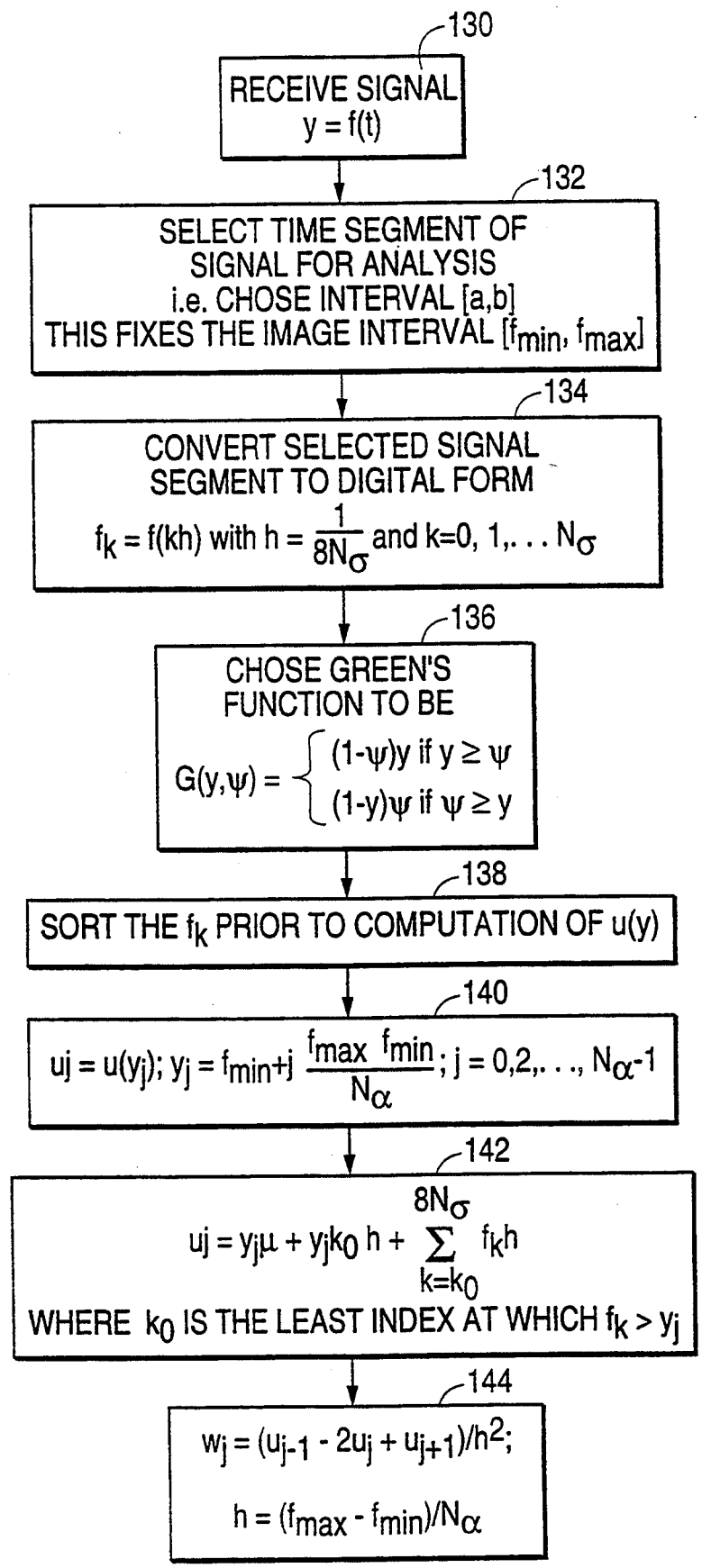
FIG. 5 is a flow diagram illustrating certain detailed numerical formulae which can be used in the accelerated Green's function approach of the embodiment illustrated in FIG. 4.

The detailed numerical formulae used in the accelerated Green's function approach of the embodiment illustrated in FIG. 4 are shown in the flow diagram sequence of FIG. 5. In the chart of FIG. 5, the first three steps 130, 132 and 134 are the same as steps 100, 102 and 104 0f FIG. 3 and steps 114, 116 and 118 of FIG. 4. In step 136, Green's function is chosen as in step 120 B of FIG. 4, which is the mathematical equivalent of step 120 A. In step 138, $f_k$ is sorted as earlier explained prior to the computation of u(y).

In step 140, $u_j=u(y_j)$ is set up and, in step 142, $u_j$ is determined by numerical methods as shown. In step 144, $w_j$ is determined on a numerical grid with spacing: $h=(f_{max}-f_{min})/N\alpha$.

In accordance with the present invention, numerical methods are used with digital signal processing to derive and compute the parameters which are utilized. As shown above in the examples, for any continuous waveform y=f(t), Green's function is used to rapidly compute the solution to the boundary value problem $u''(y)=w(y)$, $u(0)=u(1)=0$. Once the function u(y) is known, w(y) is computed from its second derivative. For the example shown in FIG. 4, the differentiation is accomplished numerically from the second central difference of the discrete expression:

$$u_j = y_j u + y_j k_o h + \frac{8N_\sigma}{\sum_{k=k_o}} f_k h \qquad \text{Eq. [11]}$$

In summary then, in a preferred embodiment of the present invention, once the selected time segment of the signal to be analyzed is converted to digital form, Green's function is preferably selected as Lu(y)=0 with selected boundary conditions and domain of definition. The domain of definition $[f_{min}, f_{max}]$ is the set of all numbers which the function f(t) takes on between $f_{min}$ and $f_{max}$. Then u(y) is determined from Green's function of f(t) and the density distribution function w(y) is then determined from Lu(y)=w(y)

Referring again to the embodiment of FIG. 1, the procedures described above, in which Green's function is utilized to determine the density distribution function and Hc, can be followed to determine the entropy Hc of both the transmitted signal 14 and the received signal 20. The respective entropies of the transmitted signal 14 and the received signal 20 may then compared to determine the effect on the transmitted signal of its passage through the medium 16. In another mode of operation, a plurality of transmitted signals are interacted with the medium, preferably in a selected scanning mode, and only the received signals are analyzed and the entropies compared with each other to determine the differences between the received signals. The method and apparatus of the present invention may be applied to any time dependent signal f(t) over any selected time interval or time intervals to determine the entropies of the signals and to compare the entropies of the signals. The signals may, for example, be electromagnetic signals of any wavelength within the full electromagnetic spectrum, including light of any wavelength, or acoustic signals transmitted as sound waves from a transducer or the like. One example is the embodiment of FIG. 2 described above. Other examples of various embodiments of the present invention are set forth below.

Figure 6:
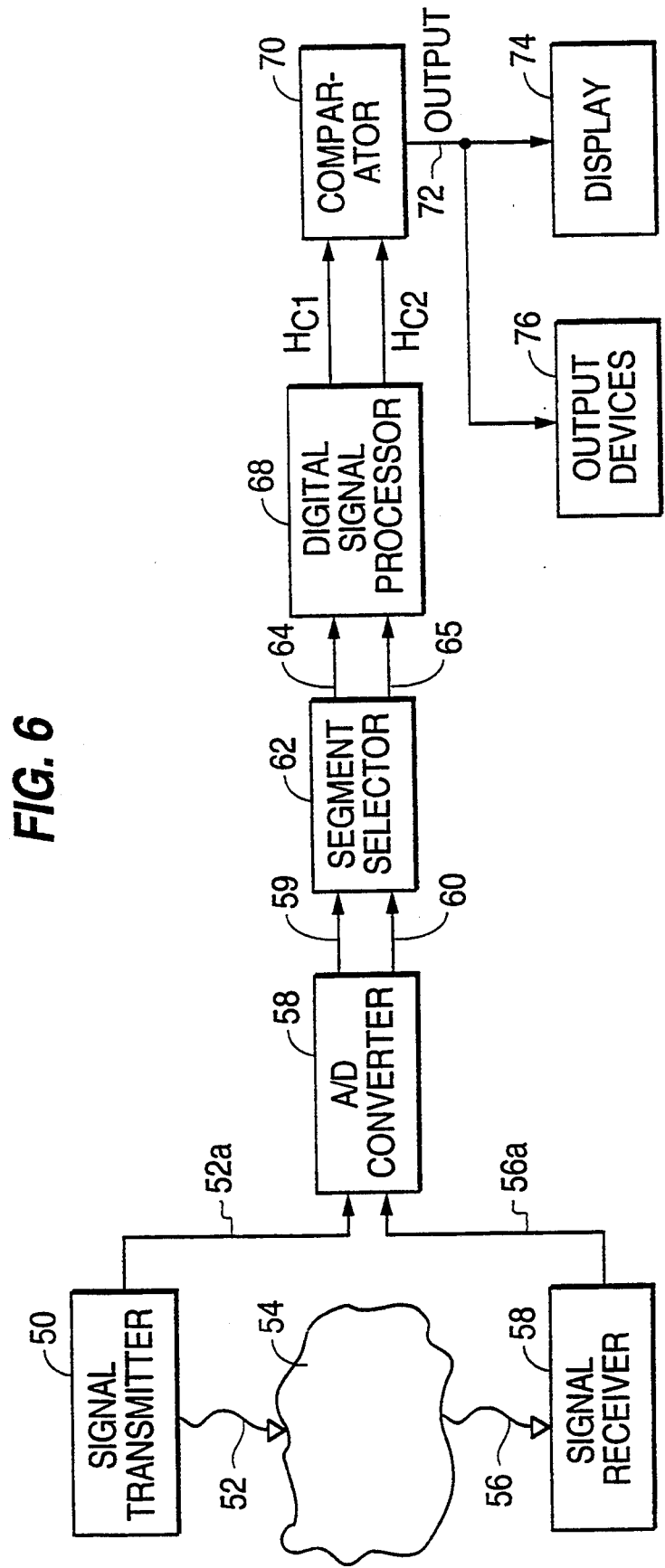
FIG. 6 is a block diagram of a signal analyzer and comparator apparatus embodying the present invention.

With reference now to FIG. 6, there is shown a complete apparatus embodying the present invention. In the embodiment of FIG. 6, a signal transmitter 50 generates and transmits a signal 52, which may, for example, be a continuous or pulsed signal of electromagnetic or acoustic form, for transmission through a medium 54. After the transmitted signal 52 travels through the medium 54, the received signal 56 is received at a receiver 58.

Figure 7:
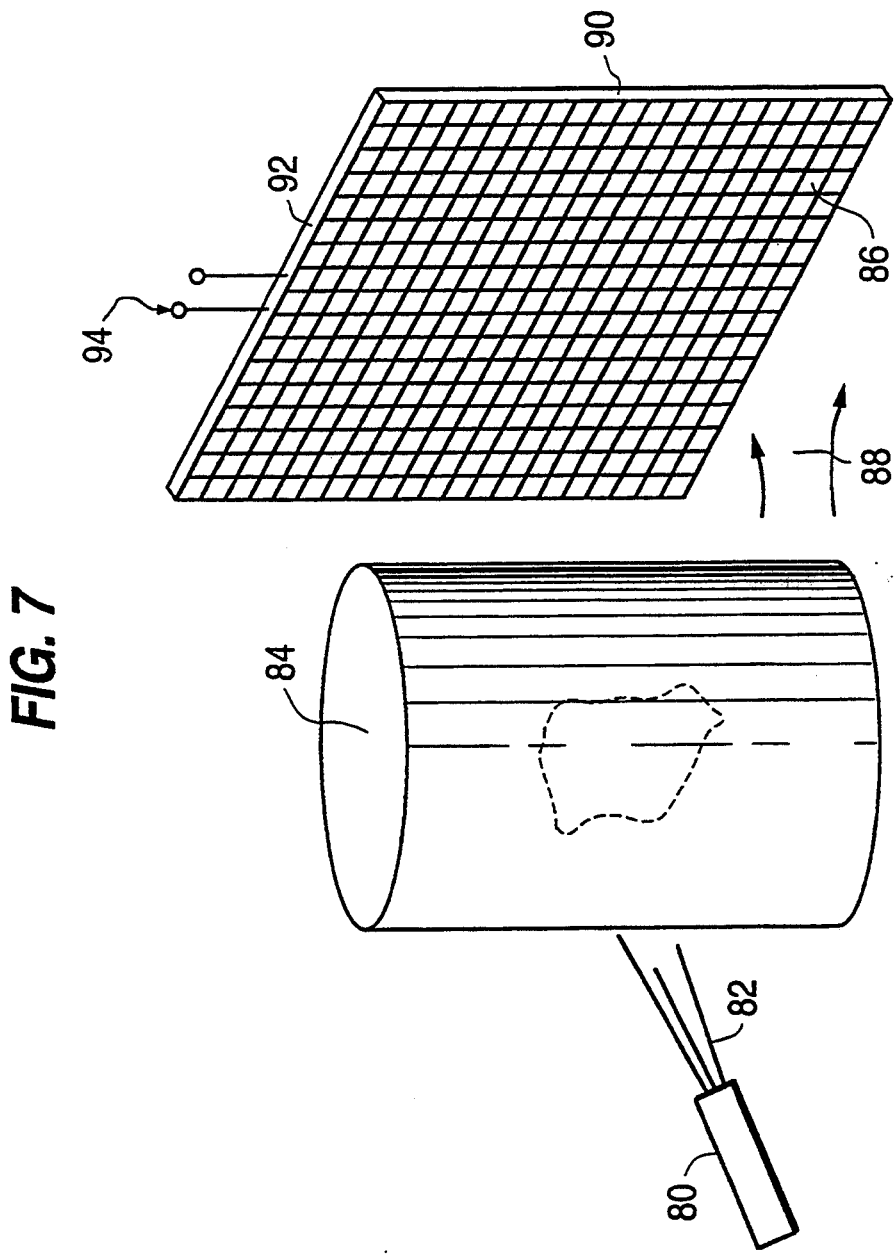
FIG. 7 is a schematic representation of an optical imaging medium probing apparatus embodying the present invention.

The signal transmitter 50 outputs a transmitted signal 52a, identical to the transmitted signal 52, for analysis. The signal receiver 58 outputs a received signal 56a, identical to the received signal 56, for analysis and comparison with the transmitted signal 52a. The transmitted signal 52a and the received signal 56a are typically initially in analog form and, in the embodiment of FIG. 7, are converted to digital form by an analog to digital (A/D) converter 58 to yield a digital transmitted signal 59 and a digital received signal 60.

The digital transmitted and received signals 59 and 60 are connected to the input of a segment selector 62, which selects a time segment of each of the signals 59 and 60 for analysis. The selected time segments of the signals 59 and 60 are for the same time segment in each case. This yields a selected time segment 64 of the digital transmitted signal 59 and a selected time segment 65 of the digital received signal 60, both for the same time segment.

The selected time segments 64 and 65 of the digital transmitted and received signals are then inputted to a digital signal processor 68 for processing according to the Green's function method of the present invention for determining the respective entropies of the selected segments 64 and 65 of the transmitted and received signals. These respective entropies are designated as $Hc_1$ and $Hc_2$ at the output of the digital signal processor 68. The digital signal processor 68 is programmed to calculate the respective density distribution functions w(y) of each of the input signal segments 64 and 65 utilizing the Green's function approach as described above and to determine in each case from w(y) the respective entropy Hc, all in accordance with the present invention.

The resulting entropies $Hc_1$ and $Hc_2$ are then sent to a comparator 70 which compares $Hc_1$ and $Hc_2$ and outputs a difference signal 72 based on the differences between the detected entropies of the transmitted signal 52/52a and received signal 56/56a. The difference signal 72 is then delivered to a display 74 for viewing and analysis and/or to other selected output devices 76.

In the embodiment of FIG. 6, the signals 52a and 56a which are inputted to the analog to digital converter 58 may both be received signals in applications where it is desired to compare the entropies of a plurality of received signals to determine comparative values and develop contrast information between the received signals. A plurality of received signals may also be inputted in sequence as the input signals 52a and 56a and the values stored in output devices 76 for comparison over a complete grid such as an x-y grid comprising a number of discrete pixel locations over an area of the medium to be analyzed.

Figure 8:
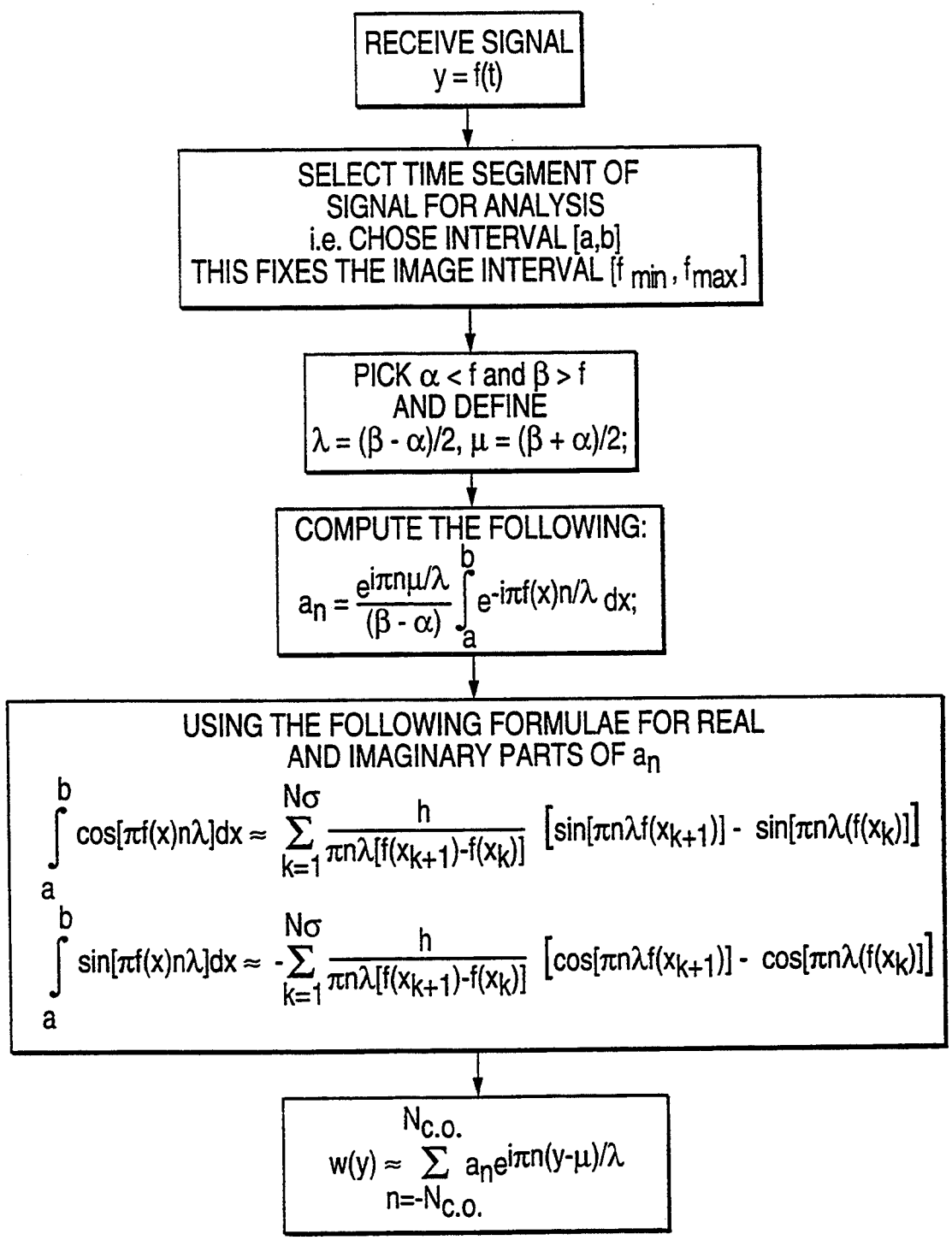
FIG. 8 is a flow diagram illustrating the steps in the Fourier series approach to the determination of signal entropy.

Another embodiment is shown in schematic form in FIG. 7. In the embodiment of FIG. 8, a light source 80 directs a beam of light 82 at a specimen 84 to be analyzed. A two-dimensional detector grid 86, which may be made up of detecting pixels arranged in an x-y grid form, detects the light 88 which passes through the specimen 84 in terms of both the amplitude of the received light signal and the position in the x-y grid at which each particular intensity is detected as a function of time.

The detected received light signals are taken off from the x-y grid of the detector 86 by means of x-y addressing connections strips 88 and 90, which in this case are outputted serially at terminals 94. Parallel output of the received signals may also be used in accordance with techniques well known in the art.

The entropies of the received light signals 88, appearing as electrical signals at terminals 94, are then determined and compared in accordance with the Green's function approach described above. That is, the received light signals 88, in the form of electrical signals at terminals 94, are introduced pixel by pixel as the received signal 56a and in each case, the entropies are determined and compared to each other to derive a pattern of any defect or other inhomogeneities or non-uniformities in the test specimen 84.

In a typical application of the embodiment of FIG. 7, the data representative of the received signals is stored in a suitable storage medium, such as in a hard magnetic disk or an optical storage disk, and the data are then run through the digital signal processor 68, which is programmed to determine the entropy of each stored received signal segment in accordance with the present invention. The respective entropies at each pixel location are then converted to gray scale values which are compared to each other, usually after normalization to a selected scale, to develop an image pattern for analysis.

In this manner, the present invention may be used with optical imaging techniques for analysis of samples or specimens or of various media.

As explained above, in the typical application of the embodiments of FIGS. 6 and 7, it is unnecessary to analyze or to determine the entropy of the transmitted signal where only comparative data are sought in relation to contrast between selected different points over an area of the test specimen to be scanned. In such a case, only the entropies of the received signals are determined and compared to each other to develop a contrast pattern based on the gray scale differences between the selected test locations in the test area. In the case of the embodiment of FIG. 7, for example, the entropies of the received signals are determined at each pixel location and the values are compared to each other to develop a gray scale pattern. The levels of the gray scale values of the pixel locations are typically normalized to a selected convenient scale for viewing and analysis.

Thus, the signals 52a and 56a which are inputted to the apparatus of the embodiment of FIG. 6 may be any first and second time dependent signals, the entropies of which are to be determined and compared to each other.

As used herein, the term "entropy" means a metric which is based upon the well known Shannon entropy and which is a determined by the integration over a selected time interval (the summation over a selected time interval in the case of numerical techniques) of the product of the density distribution function multiplied by the logarithm of the density distribution function. As used herein, the "density distribution function" means the function, as described and defined in detail in the above-mentioned references, which represents the probability that the time dependent function $y=f(t)$ will assume a particular value $y_1$ over a selected time interval from $t_1$ to $t_2$.

As noted above, the method and apparatus of the present invention provide substantial advantages over the prior art methods in which the entropy is determined using the Fourier series approach.

It will be apparent from the foregoing that the method and apparatus of the present invention provide substantial advantages over previously known signal analysis and comparison methods and apparatus, such as energy based analysis and comparison apparatus and methods as well as those methods and apparatus which utilize a Fourier series approach for determining entropy as the parameter of signal analysis and comparison. The method and apparatus of the present invention are capable of advantageous use in a wide variety of applications, some of which are described herein and others of which will occur to those skilled in the art. It is to be understood that the embodiments presented herein are set forth in detail for the purposes of making a full and clear disclosure of the same and are not to be considered as limiting in any way the true scope of the present invention as defined in the appended claims.

What is claimed is:

1. A method of comparing first and second time dependent signals to each other for deriving information from the differences resulting from the comparison comprising:

digitizing said first and second signals through an analog to digital converter and selecting for analysis time segments of said digitized first and second signals which fall within a selected time interval;

selecting a Green's function for use in analysis of said digitized first and second signal time segments;

programming and operating a digital processor to calculate the density distribution function of each of said digitized signal time segments utilizing in each case the selected Green's function and to calculate the entropy of each of said digitized signal time segments from each of said density distribution functions determined for each of said digitized signal time segments; and comparing the calculated entropies of said digitized signal time segments to determine the differences in said calculated entropies and to thereby derive information from said differences in the entropies of said digitized signal time segments.

2. The method of claim 1 wherein said first and second signals are electromagnetic signals.

3. The method of claim 2 wherein said first and second signals are light signals.

4. The method of claim 1 wherein said first and second signals are acoustic signals.

5. A method of detecting certain characteristics of a medium by means of analysis of received signals which have interacted with said medium comprising:
   generating a plurality of first signals and interacting said first signals with said medium;
   receiving as a plurality of second signals said first signals after the interaction of said first signals with said medium;
   digitizing said second signals in an analog to digital converter and selecting for analysis time segments of said digitized second signals which fall within a selected time interval;
   selecting a Green's function for use in analysis of said digitized second signal time segments;
   programming and operating a digital processor to calculate the density distribution function of each of said digitized signal time segments utilizing in each case the selected Green's function and to calculate the entropy of each of said digitized signal time segments from each of said density distribution functions determined for each of said digitized signal time segments; and
   comparing the calculated entropies of said digitized signal time segments to determine the differences in said calculated entropies and to thereby detect said certain characteristics of said medium.

6. The method of claim 5 wherein said first and second signals are electromagnetic signals.

7. The method of claim 6 wherein said first and second signals are light signals.

8. The method of claim 5 wherein said first and second signals are acoustic signals.

9. Analytical apparatus for detecting certain characteristics of a medium by analysis of received signals which have interacted with said medium comprising:
   a signal generator for generating a plurality of first signals for interaction with said medium;
   a signal transmitter for interacting said first signals with said medium;
   a signal receiver for receiving as a plurality of second signals said first signals after the interaction of said first signals with said medium;
   an analog to digital converter and selector for digitizing said second signals and for selecting for analysis time segments of said digitized second signals which fall within a selected time interval;
   digital processing means for calculating the density distribution function of each of said signal portions utilizing in each case a selected Green's function applied to said digitized second signal time segments, and for calculating the entropy of each of said signal portions from each of said density distribution functions determined for each of said signal portions; and
   a comparator for comparing the calculated entropies of said second signal time segments to determine the differences in said calculated entropies and to thereby detect said certain characteristics of said medium.

10. The analytical apparatus of claim 9 wherein said first and second signals are electromagnetic signals.

11. The analytical apparatus of claim 10 wherein said first and second signals are light signals.

12. The analytical apparatus of claim 9 wherein said first and second signals are acoustic signals.

13. A signal receiver and analyzer comprising:
   a signal receiver for receiving a signal to be analyzed;
   an analog to digital converter and selector for digitizing said received signal and for selecting for analysis a time segment of said digitized received signal which falls within a selected time interval;
   digital processing means for calculating the density distribution function of said digitized signal time segment utilizing a selected Green's function applied to said digitized signal time segments and for calculating the entropy of said selected signal portion from said density distribution function as determined for said digitized signal time segment; and
   analyzer means for analyzing the calculated entropy of said digitized signal time segment to derive information therefrom.

14. A signal receiver and analyzer as set forth in claim 13 wherein said signal receiver is adapted to receive electromagnetic signals.

15. A signal receiver and analyzer as set forth in claim 14 wherein said signal receiver is adapted to receive light signals.

16. A signal receiver and analyzer as set forth in claim 13 wherein said signal receiver is adapted to receive acoustic signals.

17. Analytical apparatus for comparing first and second time dependent signals to each other for deriving information from the differences resulting from the comparison comprising:
   an analog to digital converter and selector for digitizing said first and second signal and for selecting for analysis time segments of said digitized signals which falls within a selected time interval;
   digital processing means for calculating the density distribution function of each of said digitized signal time segments utilizing in each case a selected Green's function applied to each of said digitized signal time segments, and for calculating the entropy of each of said signal portions from each of said density distribution functions determined for each of said digitized signal time segments; and
   a comparator for comparing the calculated entropies of said digitized signal time segments to determine the differences in said calculated entropies and to thereby derive information from said determined differences in calculated entropies.

18. Analytical apparatus as set forth in claim 17 wherein said apparatus includes means for receiving electromagnetic signals.

19. Analytical apparatus as set forth in claim 18 wherein said apparatus include means for receiving light signals.

20. Analytical apparatus as set forth in claim 17 wherein said apparatus includes means for receiving acoustic signals.

21. A method of determining the entropy of a time dependent information containing signal f(t) comprising:
   receiving said time dependent signal;
   digitizing said time dependent signal in an analog to digital converter and selecting a time segment of the digitized signal for analysis;
   selecting Green's function to be $Lu(y)=0$ with selected boundary conditions and domain of definition, where L is any linear differential operator;
   setting u(y) equal to the integral over selected limits of Green's function of y and f(t); and
   programming and operating a digital processor to determine u(y) from the numerical integration of said integral of Green's function of y and f(t), to determine the density distribution function w(y) from said numerical integration and to determine the entropy of said time dependent signal from w(y).

22. The method of claim 21 including programming and operating said digital computer to sort the sampled version of f(t) given by $f_k = 0, 1, \ldots N\alpha$ into ascending or descending order prior to the step of numerical integration.

23. A method of determining the entropy of a time dependent information containing signal f(t) comprising:

receiving said time dependent signal;

digitizing said time dependent signal in an analog to digital converter and selecting a time segment of the digitized signal for analysis;

selecting Green's function to be that corresponding to $Lu(y) = d^2u(y)/dy^2$ with selected boundary conditions and domain of definition;

setting u(y) equal to the integral over selected limits of Green's function of y and f(t); and programming and operating a digital processor to determine u(y) from the numerical integration of said integral of Green's function of y and f(t), to determine the density distribution function w(y) from said numerical integration and to determine the entropy of said time dependent signal from w(y).

24. The method of claim 23 including programming and operating said digital computer to sort the sampled version of f(t) given by $f_k = 0, 1, \ldots N\alpha$ into ascending or descending order prior to the step of numerical integration.

* * * * *